United States Patent [19]
Panzera et al.

[11] Patent Number: 5,944,884
[45] Date of Patent: Aug. 31, 1999

[54] DENTAL PORCELAIN COMPOSITION

[75] Inventors: Carlino Panzera, Belle Mead; Lisa M. Kaiser, Monmouth Junction, both of N.J.

[73] Assignee: Jeneric/Pentron Incorporated, Wallingford, Conn.

[21] Appl. No.: 09/085,873

[22] Filed: May 28, 1998

Related U.S. Application Data

[60] Continuation of application No. 08/870,965, Jun. 6, 1997, which is a division of application No. 08/614,044, Mar. 12, 1996, Pat. No. 5,653,791.

[51] Int. Cl.[6] ................................................ C03C 10/10
[52] U.S. Cl. ................... 106/35; 501/6; 501/25; 501/57; 501/64; 433/202.1; 433/217.1; 433/222.1
[58] Field of Search .................. 106/35; 501/6, 501/25, 57, 64; 433/202.1, 217.1, 222.1

[56] References Cited

U.S. PATENT DOCUMENTS

| | | |
|---|---|---|
| 3,907,577 | 9/1975 | Kiefer et al. . |
| 4,042,362 | 8/1977 | MacDowell et al. . |
| 4,101,330 | 7/1978 | Burk et al. .............................. 501/143 |
| 4,278,630 | 7/1981 | Scheicher . |
| 4,455,383 | 6/1984 | Panzera . |
| 4,604,366 | 8/1986 | Kacicz et al. ............................... 501/6 |
| 4,798,536 | 1/1989 | Katz ............................................. 501/6 |
| 5,281,563 | 1/1994 | Komma et al. ........................... 501/59 |
| 5,308,391 | 5/1994 | Komma et al. ........................... 106/35 |
| 5,346,866 | 9/1994 | Komma et al. ........................... 501/59 |
| 5,453,290 | 9/1995 | Va Der Zel .............................. 106/35 |
| 5,466,285 | 11/1995 | Kamiya et al. . |
| 5,552,350 | 9/1996 | Hornor .................................... 106/35 |
| 5,698,019 | 12/1997 | Frank et al. ............................... 501/6 |

FOREIGN PATENT DOCUMENTS 2 199 027  6/1988  United Kingdom .

OTHER PUBLICATIONS

K. Krumbholz, Dreieich, *Stand und Entwicklung von Dentalkeramiken,* ZWR, 101. Jahrg. 1992, Nr. 3 (with translation).

*Primary Examiner*—Karl Group
*Attorney, Agent, or Firm*—Cantor Colburn LLP

[57] ABSTRACT

A porcelain composition for dental restorations comprising a leucite crystallite phase and a glass matrix phase, wherein the leucite crystallites possess diameters not exceeding about 10 micron. Preferably, the porcelain composition has a maturing temperature from about 750° to about 1050° C. and a coefficient of thermal expansion from about $12 \times 10^{-6}$/° C. to about $17.5 \times 10^{-6}$/° C., and comprises:

| Component | Amount (wt. %) |
|---|---|
| $SiO_2$ | 57–66 |
| $Al_2O_3$ | 7–15 |
| $K_2O$ | 7–15 |
| $Na_2O$ | 7–12 |
| $Li_2O$ | 0.5–3. |

42 Claims, No Drawings

DENTAL PORCELAIN COMPOSITION

CROSS-REFERENCE TO RELATED APPLICATIONS

This application is a continuation of U.S. application Ser. No. 08/870,965, filed Jun. 6, 1997, which is a divisional application of U.S. application Ser. No. 08/614,044, filed Mar. 12, 1996, now U.S. Pat. No. 5,653,791.

BACKGROUND OF THE INVENTION

1. Field of the Invention

This invention relates to a two-phase, dental porcelain composition for dental porcelain restorations, as well as inlays, onlays and veneers. More particularly, the present invention relates to a two-phase, low maturing temperature, high expansion feldspathic dental porcelain composition useful in the preparation and repair of dental restorations such as porcelain-fused-to metal restorations, all-ceramic restorations, inlays, onlays, and veneers.

2. Description of the Related Art

Ceramic materials have been used in dentistry in order to obtain natural-looking dental restorations such as porcelain fused-to-metal and all-ceramic restorations. Ceramics are highly desirable for this purpose since they can be colored to closely resemble the teeth they must replace, resist degradation inside the oral cavity and remain biocompatible even after years of continuous contact with mammalian tissue.

Typically, porcelain fused-to-metal (PFM) restorations are fabricated by applying a dental porcelain powder in aqueous slurry to a metal alloy frame work and firing the porcelain at high temperature to form a tight, impervious porcelain layer having the appearance of natural dentition. Those skilled in the art recognize that it is important that the firing temperature of the porcelain be at least 100° C. below the solidus temperature of the alloy used as the metal framework and that the coefficient of thermal expansion of the porcelain (in the range of room temperature to 450° C.) be only very slightly less than that of the metal so that no stress cracks are produced in the porcelain layer during firing and cooling down.

Today, there is an increasing trend in dentistry toward the use of ceramic cores in lieu of metal alloy frameworks to thus provide all-ceramic dental restorations. Where a ceramic is employed as the core of a dental restoration, any porcelain applied to the ceramic framework must possess a coefficient of thermal expansion which is slightly less than that of the ceramic to avoid production of stress cracks in the porcelain.

Metal alloys and ceramics heretofore employed in the manufacture of dental restorations have typically possessed moderately high coefficients of thermal expansion ranging from about $8 \times 10^{-6}/°C$. to about $14 \times 10^{-6}/°C$. However, alloys and ceramics possessing coefficients of thermal expansion of as high as about $18 \times 10^{-6}/°C$. are increasingly being used.

In commonly assigned, copending U.S. application Ser. No. 08/532,179 filed Sep. 22, 1995, the contents of which are incorporated by reference herein, a dental porcelain composition is described which is amorphous, i.e., single phase, and which possess a moderately high coefficient of thermal expansion closely matching those of conventional alloys and ceramics heretofore employed in the manufacture of dental restorations. This composition is advantageously applied to such conventional alloys and ceramics to provide an extremely smooth, fused glassy surface on the resulting dental restorations. However, the coefficient of thermal expansion of the single-phase, amorphous dental porcelain described in U.S. application Ser. No. 08/532,179 is too low to be applied to high expansion alloys and porcelains.

A need exists, therefore, for a dental porcelain composition which can be fused to high expansion alloys and ceramics, i.e., those possessing high coefficients of thermal expansion of as high as about $18 \times 10^{-6}/°C$., to thus provide an extremely smooth surface thereon. An example of a high expansion ceramic is OPTEC™ porcelain available from Jeneric/Pentron, Inc. Wallingford, Conn. OPTEC porcelain possesses a high crystalline leucite ($K_2O \cdot Al_2O_3 \cdot 4SiO_2$) content wherein the leucite crystallites broadly range in diameter from about 0.5 microns to as high as about 40 microns.

Accordingly, it is an object of the present invention to provide a dental porcelain composition which is especially suitable for the preparation and repair of dental restorations, as well as inlay, onlays, and veneers, in applications involving high expansion alloys and/or ceramics.

It is another object of the present invention to provide a dental porcelain possessing a maturing temperature ranging from about 650° C. to about 1050° C. and a coefficient of thermal expansion (room temperature to 450° C.) of from about $12 \times 10^{-6}/°C$. to about $17.5 \times 10^{-6}/°C$., which is chemically and thermally stable and which provides a smooth, non-abrasive surface when applied to high expansion alloys and ceramics.

SUMMARY OF THE INVENTION

These as well as other objects and advantages are accomplished by the present invention which relates to a two-phase porcelain composition comprising a leucite crystallite phase dispersed in a feldspathic glass matrix, a maturing temperature of from about 650° C. to about 1050° C. and a coefficient of thermal expansion (room temperature to 450° C.) of from about $12 \times 10^{-6}/°C$. to about $17.5 \times 10^{-6}/°C$., said porcelain composition comprising:

| Component | Amount (wt. %) |
| --- | --- |
| $SiO_2$ | 57–66 |
| $Al_2O_3$ | 7–15 |
| $K_2O$ | 7–15 |
| $N_2O$ | 7–12 |
| $Li_2O$ | 0.5–3 |
| $CaO$ | 0–3 |
| $MgO$ | 0–7 |
| F | 0–4 |
| $CeO_2$ | 0–1 | wherein the leucite crystallites possess diameters not exceeding about 10 microns and represent from about 5 to about 65 percent of the two-phase porcelain composition.

It is essential to the practice of the present invention that the leucite crystallites present in the two-phase porcelain composition herein possess diameters not exceeding about 10 microns. Diameters in excess of about 10 microns will impart an undesirably rough and uneven surface to the composition when employed in its intended environment of use. Indeed, it has been determined that leucite diameters above about 10 microns may wear away local dentition and cause discomfort/irritation inside the oral cavity.

DETAILED DESCRIPTION OF THE INVENTION

The two-phase porcelain composition of the present invention can be used to form dental restorations in accordance with procedures that are well known in the art. Thus, the porcelain composition herein can be employed in the manufacture of a PFM restoration which utilizes a high expansion metal alloy or in the manufacture of a high expansion all-ceramic restoration. The porcelain composition of the present invention can also be used as a glaze which can be fused to high expansion ceramics to impart a shiny, smooth surface thereto when it is necessary or desirable to achieve such a surface at a low maturing temperature, e.g., at about 800° C., instead of the natural shine normally obtained at about 925° to 960° C.

The two-phase dental porcelain composition of the present invention comprises:

| Oxide | Range | Preferred | Example 1 | Example 2 |
|---|---|---|---|---|
| $SiO_2$ | 57–66 | 58–65 | 62.1 | 58.0 |
| $Al_2O_3$ | 7–15 | 8–14 | 9.8 | 14.0 |
| $K_2O$ | 7–15 | 11–15 | 14.2 | 15 |
| $Na_2O$ | 7–12 | 7.5–11 | 7.6 | 8.1 |
| $Li_2O$ | 0.5–3 | 0.7–1.5 | 1.1 | 1.5 |
| CaO | 0–3 | 0–1.5 | 1.0 | 1.0 |
| MgO | 0–7 | 0–5 | 1.9 | 1.0 |
| F | 0–4 | 0–3 | 1.9 | 1.0 |
| $CeO_2$ | 0–1 | 0–0.5 | 0.4 | 0.4 |
| Coefficient of thermal expansion (RT to 450° C.) ($\times 10^{-6}$/°C.) | 12–17.5 | 12–17.5 | 15.0 | 17.4 |
| Maturing Temperature (°C.) | 750–1050 | 800–1000 | 815 | 850 |
| Maturing Temperature (°F.) | 1318–1922 | 1472–1832 | 1500 | 1562 |

The dental porcelain composition of the present invention is a two-phase glass which contains a leucite crystallite phase dispersed in a feldspathic glass matrix. The leucite crystallites are present in an amount ranging from about 5 to about 65 weight percent based on the weight of the entire composition. In the practice of the present invention, the leucite crystallites present in the composition possess diameters not exceeding about 10 microns, preferably not exceeding about 5 microns, more preferably not exceeding about 1 micron.

In one embodiment of the present invention, the two-phase dental porcelain composition is derived from a blend of a first porcelain component possessing a low fusing temperature and a moderately high coefficient of thermal expansion, such as the porcelain disclosed in copending U.S. application Ser. No. 08/532,179, with a second porcelain component possessing a high coefficient of thermal expansion and containing a dispersed crystalline leucite phase wherein the leucite crystallites are less than about 10 microns in diameter. The first porcelain component and second porcelain component are typically blended in a weight ratio of from about 95:5 to about 70:30 to provide a mixture which is then fired at about 850° C. to form the porcelain composition of this invention.

The introduction of leucite crystallites in the porcelain composition of this invention raises the coefficient of thermal expansion of the porcelain composition. The porcelain forms a chemical bond with high expansion alloys and ceramics such as Optec™ porcelain when fused thereto and exhibits a thermal expansion which is about 0.5 to $1.5 \times 10^{-6}$/°C. lower than the thermal expansion of such high expansion alloys or ceramics. The resulting fused restoration is thereby placed in slight compression when cooled to room temperature.

The porcelain composition herein has sufficient viscosity at the maturing temperature such that it does not lose its shape yet fires to nearly 100% of theoretical density, thus forming a tight, impervious surface necessary in the oral environment. The fused surface is also nearly perfectly smooth providing a slippery, thus kinder environment to opposing natural dentition than that typically provided by conventional porcelains.

The first porcelain component described above is known and can be prepared in accordance with well known procedures. A particularly preferred first porcelain component which can be employed herein is described in the aforementioned U.S. application Ser. No. 08/532,179. Porcelains such as SYNSPAR® porcelain and PENCRAFT PLUS™ porcelain (available from Jeneric/Pentron Incorporated of Wallingford, Conn.), CERAMCO porcelain (available from Ceramco, Inc. of Burlington, N.J.), and the like, which typically exhibit coefficients of thermal expansion ranging from about $10 \times 10^{-6}$/°C. to about $14 \times 10^{-6}$/°C. (room temperature to 450° C.) can be suitably employed as the first porcelain component.

The preparation of such materials is well known in the art. Ceramic precursors such as silica, alumina, feldspar, calcium carbonate, sodium carbonate, potassium carbonate, or if desired, the actual oxides, are blended, preferably in finely divided powder form such as powder sufficiently fine to pass through a 200 mesh screen (Tyler series), and fused at a temperature of at least about 1200° C., and preferably at least about 1400° C., in a crucible to form a glass. The molten glass is then quenched in water, dried, and ground in a ball mill to provide the first porcelain component in the form of a powder. It is preferred that the powder is ground finely enough so that it will pass through a 200 mesh screen (Tyler series).

The first porcelain component utilized herein preferably will possess a fusing temperature of from about 760 to about 815° C. and a coefficient of thermal expansion of from about $10.6 \times 10^{-6}$/°C. to about $11.6 \times 10^{-6}$/°C.

The second porcelain component of this invention is preferably produced in accordance with the teachings of commonly assigned U.S. Pat. No. 4,798,536, the contents of which are incorporated by reference herein. In accordance therewith, a feldspar, wherein at least a portion of the $K_2O$, $Al_2O_3$, and $SiO_2$ is employed as a precursor to the formation of leucite ($K_2O \cdot Al_2O_3 \cdot 4SiO_2$) dispersed in glass and is the second porcelain component. While not wishing to be bound by theory, it is believed that such leucite crystallites function as nuclei which initiate and promote nucleation and growth in the magma of additional leucite crystallites during the fusing and cooling stages of production. As the magma is cooled, the crystalline leucite becomes less soluble and precipitates out. In accordance with the method of the '536 patent, a feldspar containing crystalline leucite is culled to remove quartz, mica, biotite, etc., ground to a fine powder, passed through a magnetic separator to remove iron impurities, further ground, blended with other desired components, fused at about 2150 to about 2350° F. and cooled to form a vitreous body containing a uniform dispersion of leucite crystallites. The fused, cooled porcelain is then crushed and reduced to a fine powder which can pass through a 180 to 200 mesh screen. The second porcelain component preferably possesses a coefficient of thermal expansion of from about $16 \times 10^{-6}$/°C. to about $17.5 \times 10^{-6}$/°C.

In accordance with the practice of the present invention, the second porcelain component, prior to being combined or blended with the first porcelain component, is treated to separate and isolate leucite crystallites possessing diameters not exceeding about 10 microns. Leucite crystallized possessing diameters not exceeding about 10 microns will impart extremely smooth surfaces to dental restorations produced with the porcelain composition of this invention. The second porcelain component can be treated by mixing the second porcelain component in powder form, such as powder sufficiently fine to pass through a 200 mesh screen (Tyler series), with water in a suitable vessel, allowing the mixture to settle, decanting and retaining the supernatant liquid, mixing the retained supernatant liquid with water in a suitable vessel, allowing the mixture to settle a second time, decanting and retaining the supernatant liquid, evaporating the water of the retained supernatant liquid to provide dried powder and screening the dried powder through 325 (or greater) mesh screen (Tyler series) to break up any agglomerates. By virtue of the foregoing treatment, leucite crystallites possessing diameters not exceeding about 10 microns will be separated and isolated from the second porcelain component. It will be understood by those skilled in the art that variations of the foregoing treatment method or other treatment methods or combinations thereof such as jet milling, air classification, floatation, etc. can be employed herein to separate and isolate the small diameter leucite crystallites.

The properties of the first and second porcelain components can be adjusted by applying well known principles. For example, the coefficient of thermal expansion of either component can be increased, if desired, by decreasing the proportion of $SiO_2$ and/or increasing the proportion of the alkali metal oxides. As is taught in U.S. Pat. No. 4,798,536, more or less flux (e.g., potassium, lithium, calcium and magnesium compounds) will increase or decrease the fusing point of the resultant porcelain composition. The fusion point of either component can be reduced by increasing the proportion of CaO, and/or the alkali metal oxides. An increase in the $Na_2O:K_2O$ ratio also lowers the fusion point. It is well within the skill of the ceramics art to apply these principles to make fine adjustments to the thermal expansion coefficients and fusion temperatures of either component used in the manufacture of the porcelain composition herein.

If desired, in order to assure proper aesthetics, one or more layers of the porcelain composition of the present invention can be applied over a high expansion metal alloy or ceramic core with each layer being separately fired. Thus, for example, an opaque layer containing an opacifying agent such as $TiO_2$, $SnO_2$, $Al_2O_3$, ZnO, $CeO_2$, and the like can be applied over the framework and fired. Thereafter, or in lieu thereof, or in combination therewith, a shaded layer can be applied containing one or more conventional pigments such as vanadates, manganates, chromates, or other transition metal compounds, to tint the shaded layer to the desired shade. If desired, a fluorescing agent such as cerium oxide, terbium oxide, yttrium oxide, and the like, or other conventional additives can also be incorporated into the porcelain to simulate natural dentition. The opaque and/or fluorescent shaded layer(s) can then be overcoated (before or after firing), if desired, with the porcelain composition of the present invention. In this manner, special effects can be obtained, e.g., a different shade at the tip of the restoration than at the gingival area. The porcelain layers can be applied to the framework in the usual manner, as by applying a paste of the porcelain powder in water over the framework, shaping to the desired configuration, and then firing.

The present invention can also be used by itself as an inlay/onlay material to replace amalgam, gold or other ceramics. The porcelain of the present invention can be prepared as an inlay/onlay or veneer by building the porcelain powder in the form of an aqueous slurry on an appropriate refractory investment die (such as SYNVEST™ sold by Jeneric/Pentron Incorporated of Wallingford, Conn.) and then firing the porcelain/die combination to 815°–850° C. to effect proper maturation of the porcelain. If desired, those skilled in the art can also use foil techniques which utilize a thin (0.001") piece of platinum or other suitable foil adapted to a gypsum die to hold the porcelain in its proper geometry, remove the foil/porcelain from the gypsum die and fire as before to effect proper fusion of the porcelain. The resultant sample would be placed in the prepared cavity and would result in a smooth surface in contact with the natural dentition.

Further variations and modifications of the present invention will become apparent to those skilled in the art from the foregoing and are intended to be encompassed by the claims appended hereto.

What is claimed is:

1. A porcelain composition comprising a leucite crystallite phase and a glass matrix phase, the leucite crystallites possessing diameters not exceeding about 10 microns and representing from about 5 to about 65 weight percent of the porcelain composition, and wherein the porcelain composition comprises:

| Component | Amount (wt. %) |
| --- | --- |
| $SiO_2$ | 58–65 |
| $Al_2O_3$ | 7–15 |
| $K_2O$ | 7–15 |
| $Na_2O$ | 7–12 |
| $Li_2O$ | 0.5–3. |

2. The porcelain composition of claim 1 wherein the porcelain composition has a coefficient of thermal expansion of from about $12\times10^{-6}/°C.$ to about $17.5\times10^{-6}/°C.$ (room temperature to 450° C.).

3. The porcelain composition of claim 1 wherein the porcelain composition has a maturing temperature of from about 750° to about 1050° C.

4. The porcelain composition of claim 3 wherein the porcelain composition has a coefficient of thermal expansion of from about $12\times10^{-6}/°C.$ to about $17.5\times10^{-6}/°C.$ (room temperature to 450° C.).

5. The porcelain composition of claim 1 wherein the porcelain composition has a maturing temperature in the range from about 800° to about 1000° C.

6. The porcelain composition of claim 5 wherein the porcelain composition has a coefficient of thermal expansion of from about $12\times10^{-6}/°C.$ to about $17.5\times10^{-6}/°C.$ (room temperature to 450° C.).

7. The porcelain composition of claim 1 wherein said glass matrix phase comprises a feldspathic glass matrix.

8. The porcelain composition of claim 1 wherein said porcelain composition further includes at least one or more of the following:

| Component | Amount (wt %) |
| --- | --- |
| CaO | up to 3 |
| MgO | up to 7 |
| F | up to 4 |
| $CeO_2$ | up to 1. |

9. The porcelain composition of claim 1 wherein said porcelain composition further comprises:

| Component | Amount (wt. %) |
|---|---|
| CaO | 0–1.5 |
| MgO | 0–5 |
| F | 0–3 |
| $CeO_2$ | 0–0.5. |

10. A porcelain composition comprising a leucite crystallite phase and a glass matrix phase, the leucite crystallites possessing diameters not exceeding about 10 microns and representing from about 5 to about 65 weight percent of the porcelain composition, and wherein said porcelain composition comprises:

| Component | Amount (wt. %) |
|---|---|
| $SiO_2$ | 58–65 |
| $Al_2O_3$ | 8–14 |
| $K_2O$ | 11–15 |
| $Na_2O$ | 7.5–11 |
| $Li_2O$ | 0.7–1.5. |

11. The porcelain composition of claim 10 wherein said porcelain composition further includes at least one or more of the following:

| Component | Amount (wt %) |
|---|---|
| CaO | up to 1.5 |
| MgO | up to 5 |
| F | up to 3 |
| $CeO_2$ | up to 0.5. |

12. The porcelain composition of claim 10 wherein said porcelain composition further comprises at least one or more of the following:

| Component | Amount (wt. %) |
|---|---|
| CaO | 0–1.5 |
| MgO | 0–5 |
| F | 0–3 |
| $CeO_2$ | 0–0.5. |

13. The porcelain composition of claim 1 further comprising at least one component selected from the group consisting of opacifying agents, pigments, and fluorescing agents.

14. A dental restoration comprising a high expansion metal alloy or ceramic framework and at least one coating fused thereon of the porcelain composition of claim 1.

15. A porcelain fused to metal dental restoration comprising a metallic framework, at least one coating of a high expansion ceramic fused thereto, and a glaze which at least partially covers said ceramic, fused thereto below about 900° C. comprising the porcelain composition of claim 1.

16. An inlay, onlay or veneer comprising the porcelain composition of claim 1.

17. A method of manufacturing a dental porcelain composition comprising a leucite crystallite phase and a glass matrix phase, the dental porcelain composition comprising

| Component | Amount (wt. %) |
|---|---|
| $SiO_2$ | 57–66 |
| $Al_2O_3$ | 7–15 |
| $K_2O$ | 7–15 |
| $Na_2O$ | 7–15 |
| $Li_2O$ | 0.5–3; and | wherein the leucite crystallites possess diameters not exceeding about 10 microns and represent from about 5 to about 65 weight percent of the dental porcelain composition, comprising blending a first porcelain component having a coefficient of thermal expansion in the range from about $10 \times 10^{-6}$/°C. to about $14 \times 10^{-6}$/°C. with a second porcelain component having a coefficient of thermal expansion in the range from about $16 \times 10^{-6}$/°C. to about $17.5 \times 10^{-6}$/°C. and comprising leucite crystallites having diameters not greater than about 10 microns to form a dental porcelain mixture; and firing the mixture at a temperature in the range from about 750° C. to about 1150° C., thereby producing the dental porcelain composition comprising the leucite crystallites.

18. The porcelain composition of claim 1, wherein the leucite crystallites possess diameters not exceeding about 5 microns.

19. The porcelain composition of claim 10, wherein the leucite crystallites possess diameters not exceeding about 5 microns.

20. The porcelain composition of claim 10, wherein the porcelain composition has a coefficient of thermal expansion of from about $12 \times 10^{-6}$/°C. to about $17.5 \times 10^{-6}$/°C. (room temperature to 450° C.).

21. The porcelain composition of claim 10 wherein the porcelain composition has a maturing temperature of from about 750° to about 1050° C.

22. The porcelain composition of claim 21, wherein the porcelain composition has a coefficient of thermal expansion of from about $12 \times 10^{-6}$/°C. to about $17.5 \times 10^{-6}$/°C. (room temperature to 450° C.).

23. The porcelain composition of claim 10, wherein the porcelain composition has a maturing temperature in the range from about 800° to about 1000° C.

24. The porcelain composition of claim 23, wherein the porcelain composition has a coefficient of thermal expansion of from about $12 \times 10^{-6}$/°C. to about $17.5 \times 10^{-6}$/°C. (room temperature to 450° C.).

25. The porcelain composition of claim 10, further comprising at least one component selected from the group consisting of opacifying agents, pigments, and fluorescing agents.

26. A dental restoration comprising a high expansion metal alloy or ceramic framework and at least one coating fused thereon of the porcelain composition of claim 10.

27. The restoration of claim 26, wherein the framework comprises a ceramic.

28. A porcelain fused to metal dental restoration comprising a metallic framework, at least one coating of a high expansion ceramic fused thereto, and a glaze which at least partially covers said ceramic, fused thereto below about 900° C. comprising the porcelain composition of claim 10.

29. An inlay, onlay or veneer comprising the porcelain composition of claim 10.

30. The method of claim 17 wherein the dental porcelain mixture is fired at a temperature of from about 780° to about 870° C.

31. The method of claim 17 wherein the first porcelain component possesses a coefficient of thermal expansion (room temperature to 450° C.) of from about $10.6 \times 10^{-6}/°C$. to about $11.6 \times 10^{-6}/°C$.

32. The method of claim 17 wherein the first porcelain component possesses a fusing temperature of from about 760° to about 815° C.

33. The method of claim 17 wherein the first porcelain component is blended with the second porcelain component in a weight ratio of from about 95:5 to about 70:30 to form the dental porcelain mixture.

34. The method of claim 17 wherein the leucite crystallites possess diameters not exceeding about 5 microns.

35. The method of claim 17, wherein the dental porcelain composition further includes at least one of the following:

| Component | Amount (wt %) |
|---|---|
| CaO | 0–1.5 |
| MgO | 0–5 |
| F | 0–3 |
| $CeO_2$ | 0–0.5. |

36. The method of claim 17, wherein the dental porcelain composition comprises:

| Component | Amount (wt. %) |
|---|---|
| $SiO_2$ | 58–65. |

37. The method of claim 36, wherein the dental porcelain composition further includes at least one of the following:

| Component | Amount (wt %) |
|---|---|
| CaO | 0–1.5 |
| MgO | 0–5 |
| F | 0–3 |
| $CeO_2$ | 0–0.5. |

38. The method of claim 17 wherein the dental porcelain composition comprises:

| Component | Amount (wt. %) |
|---|---|
| $SiO_2$ | 58–65 |
| $Al_2O_3$ | 8–14 |
| $K_2O$ | 11–15 |
| $N_2O$ | 7.5–11 |
| $Li_2O$ | 0.7–1.5. |

39. The method of claim 38, wherein the dental porcelain composition further includes at least one of the following:

| Component | Amount (wt %) |
|---|---|
| CaO | 0–1.5 |
| MgO | 0–5 |
| F | 0–3 |
| $CeO_2$ | 0–0.5. |

40. A dental restoration fabricated from a dental porcelain composition manufactured by the method of claim 17.

41. A dental restoration fabricated from a dental porcelain composition manufactured by the method of claim 35.

42. A dental restoration fabricated from a dental porcelain composition manufactured by the method of claim 38.

* * * * *